United States Patent
Tano et al.

(10) Patent No.: US 8,249,716 B2
(45) Date of Patent: Aug. 21, 2012

(54) SIGHT REGENERATION ASSISTING DEVICE

(75) Inventors: Yasuo Tano, Kobe (JP); Hirokazu Sakaguchi, Minoo (JP); Eiji Yonezawa, Okazaki (JP); Ryoko Tano, legal representative, Kobe (JP); Ryotaro Tano, legal representative, Kobe (JP); Kojiro Tano, legal representative, Kobe (JP); Sayaka Nakajima, legal representative, Kobe (JP)

(73) Assignee: Nidek Co., Ltd., Gamagori-shi (JP)

( * ) Notice: Subject to any disclaimer, the term of this patent is extended or adjusted under 35 U.S.C. 154(b) by 64 days.

(21) Appl. No.: 12/448,503

(22) PCT Filed: Dec. 27, 2007
(Under 37 CFR 1.47)

(86) PCT No.: PCT/JP2007/075098
§ 371 (c)(1),
(2), (4) Date: Mar. 12, 2010

(87) PCT Pub. No.: WO2008/084711
PCT Pub. Date: Jul. 17, 2008

(65) Prior Publication Data
US 2010/0222842 A1  Sep. 2, 2010

(30) Foreign Application Priority Data

Dec. 27, 2006  (JP) ................................ 2006-350771

(51) Int. Cl.
*A61N 1/36* (2006.01)
(52) U.S. Cl. ........................... 607/54; 607/115; 607/141
(58) Field of Classification Search .................... 607/46, 607/53, 54, 115, 116, 141
See application file for complete search history.

(56) References Cited

U.S. PATENT DOCUMENTS

| | | | |
|---|---|---|---|
| 2002/0091422 A1* | 7/2002 | Greenberg et al. | 607/54 |
| 2005/0080473 A1 | 4/2005 | Gibson et al. | |
| 2006/0058857 A1* | 3/2006 | Tano et al. | 607/54 |

FOREIGN PATENT DOCUMENTS

| | | |
|---|---|---|
| JP | 02-277468 | 11/1990 |
| JP | 05-503454 | 6/1993 |
| JP | 11-047286 | 2/1999 |
| JP | 2001-518828 | 10/2001 |
| JP | 2004-181100 | 7/2004 |
| JP | 2004-534567 | 11/2004 |
| WO | WO 91/11215 A1 | 8/1991 |
| WO | WO 98/42405 A1 | 10/1998 |
| WO | WO 2004/049986 A1 | 6/2004 |

\* cited by examiner

*Primary Examiner* — Carl H Layno
*Assistant Examiner* — Pamela M Bays
(74) *Attorney, Agent, or Firm* — Oliff & Berridge, PLC (57) ABSTRACT

A sight regeneration assisting device for regenerating the sight of a patient comprises a plurality of needlelike electrodes each having a pointed distal end and being to be inserted in an optic papilla of a patient's eye in use; and a signal generator connected with the electrodes through a conductive wire to generate an electric stimulus pulse signal to be outputted from the electrodes, each of the electrodes, excepting a predetermined portion including the distal end, being coated with a coating layer made of resin exhibiting good biocompatibility and insulation, and the coating layer being formed with a turn-back retaining portion for retaining the electrode.

5 Claims, 9 Drawing Sheets

SIGHT REGENERATION ASSISTING DEVICE

TECHNICAL FIELD

The present invention relates to a sight regeneration assisting device for regenerating the sight (vision).

BACKGROUND ART

Recently, various devices have been proposed for regenerating the sight (vision) of a blind patient. For instance, there is proposed a device for regenerating the sight of a patient by imparting electric stimulus from an optic papilla of the blind patient (see US 2006/0058857A (WO 2004/049986A)).

In the device arranged to electrically stimulate nerve fibers by an electrode implanted (inserted) in the optic papilla as mentioned above, it is important that the electrode is stably implanted in the optic papilla for a long term without coming off. In the case where a plurality of electrodes is implanted, it is preferable to discriminate them individually.

CITATION LIST

Patent Literature 1: US 2006/0058857A

SUMMARY OF INVENTION

Technical Problem

The present invention has a purpose to provide a sight regeneration assisting device capable of stably electrically stimulating nerve fibers.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

Solution to Problem

To achieve the purpose of the invention, there is provided a sight regeneration assisting device for regenerating sight of a patient, comprising: a plurality of needlelike electrodes each having a pointed distal end and being to be inserted in an optic papilla of a patient's eye in use; and a signal generator connected with the electrodes through a conductive wire to generate an electric stimulus pulse signal to be outputted from the electrodes, each of the electrodes, excepting a predetermined portion including the distal end, being coated with a coating layer made of resin exhibiting good biocompatibility and insulation, and the coating layer being formed with a turn-back retaining portion for preventing the electrode from coming off.

In the above sight regeneration assisting device, preferably, the retaining portion is made of resin integral with the coating layer.

In the above sight regeneration assisting device, preferably, the conductive wire is formed with a flat portion which will be placed in a vitreous body when the electrode is inserted in the optic papilla.

In the above sight regeneration assisting device, preferably, the conductive wire includes electrode discrimination means in a portion which will be placed in a vitreous body when the electrode is inserted in the optic papilla.

In the above sight regeneration assisting device, preferably, the conductive wire is coated with a coating layer made of resin exhibiting good biocompatibility and insulation, and the electrode discrimination means is formed by use of the coating layer that coats the conductive wire.

REFERENCE SIGNS LIST

1 Sight regeneration assisting device
10 Extracorporeal device
11 Visor
12 Photographing unit
13 External unit
14 Primary coil
20 Intracorporeal device
21 Secondary coil
22 Process control part
23 Electrode
23a Electrode portion
23b Retaining portion
23c Implanted portion
24 Conductive wire
30 Indifferent electrode
100 Processing unit
102 Signal converting part
103 Setting part
110 Power supply unit
200 Electrode discrimination portion
210 Coating layer
300 Masking member

DESCRIPTION OF EMBODIMENTS

Figure 1:
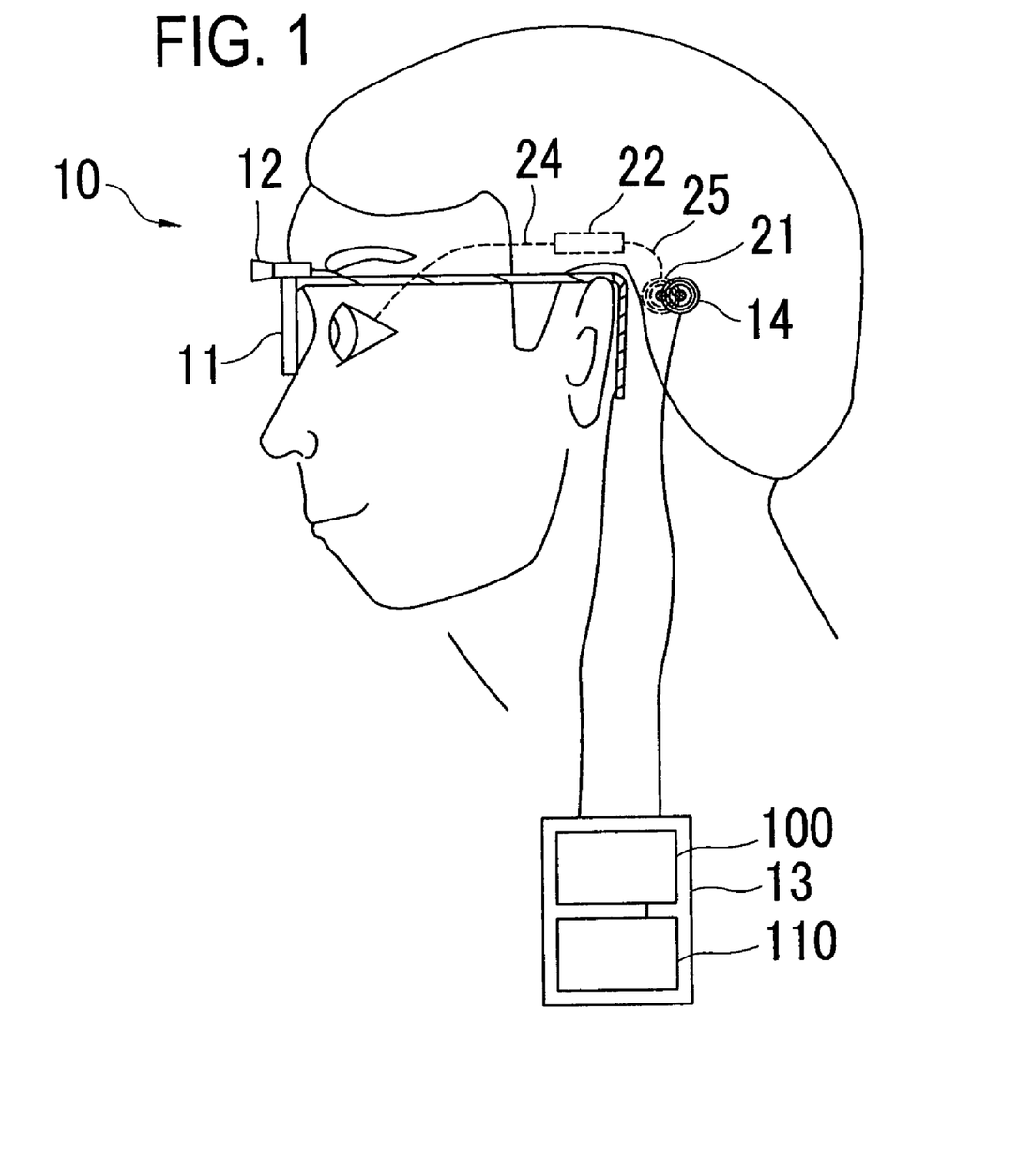
FIG. 1 is a view showing a using state of a sight regeneration assisting device in an embodiment of the invention.
Figure 2:
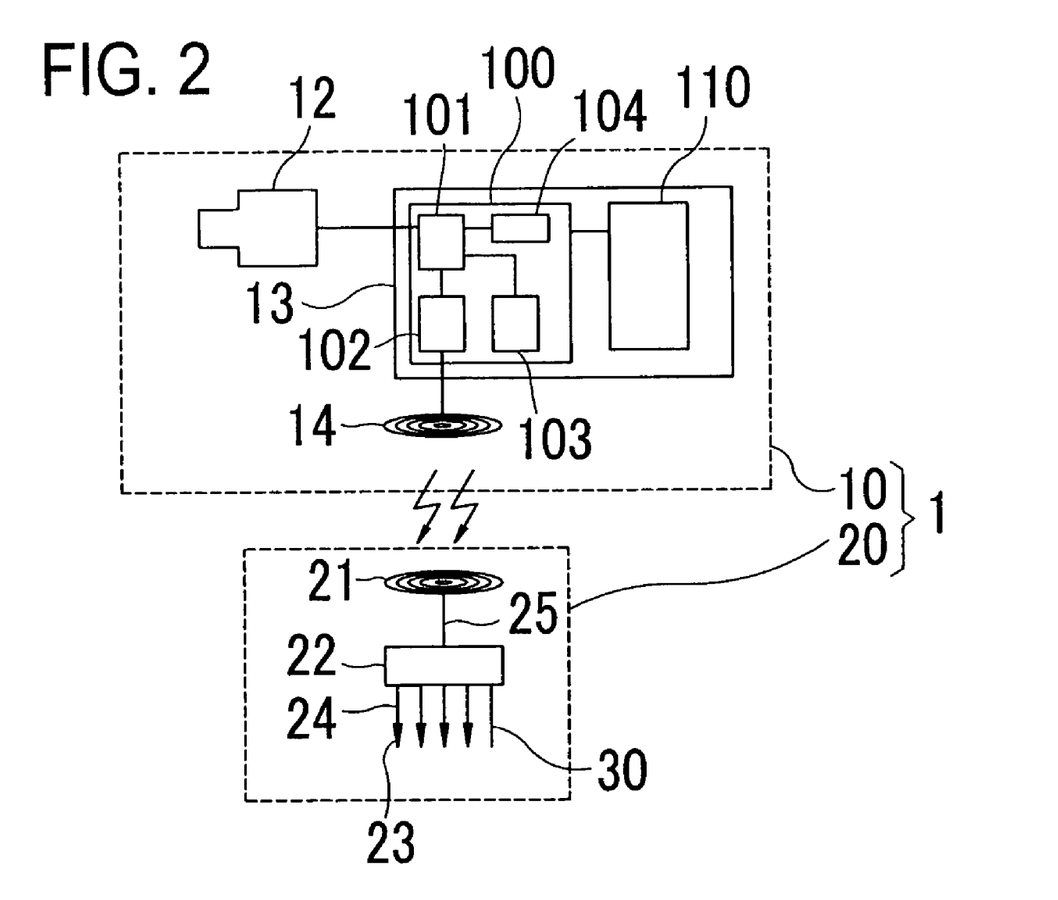
FIG. 2 is a block diagram showing a schematic configuration of the sight regeneration assisting device.

A detailed description of a preferred embodiment of the present invention will now be given referring to the accompanying drawings. FIG. 1 is a view showing a using state of a sight regeneration assisting device in the embodiment of the present invention and FIG. 2 is a block diagram showing a schematic configuration of the sight regeneration assisting device. The sight regeneration assisting device 1 includes an extracorporeal device 10 and an intracorporeal device 20.

The extracorporeal device 10 includes a visor 11 to be worn by a patient, a photographing unit 12 having a CCD camera and others attached to the visor 11, an external unit 13, and a primary coil (a transmission unit) 14. The visor 11 has an eyeglass shape and is worn in front of patient's eyes in use. The photographing unit 12 is attached to the front surface of the visor 11 to photograph an object to be recognized by the patient.

The external unit 13 includes a processing unit 100 and a power supply unit (a battery) 110 connected to the processing unit 100 to supply electric power to the device 1 (the extracorporeal device 10 and the intracorporeal device 20). The processing unit 100 includes a control part 101 comprising a CPU and others, a signal converting part 102 for image-processing image data from the photographing unit 12 and converting it into data for electric stimulus pulse signal (hereinafter, referred to as a stimulus signal), a setting part 103, and a storage part 104. The photographing unit 12, the signal converting part 102, the setting part 103, and the storage part 104 are connected to the control part 101. The primary coil 14 is connected to the signal converting part 102.

The setting part 103 has various operation buttons (an input part) and is used for setting an output condition (hereinafter, also referred to as a stimulus condition) of a stimulus signal to be outputted from electrodes 23 mentioned later, and others. Furthermore, the setting part 103 is used for recording, in association with the stimulus conditions and others, appearance (generation) positions and shapes (mainly, sizes) of light perceptions (artificial light perceptions, intraocular photesthesia) without light stimulus, called phosphenes, which are perceived by a patient when a stimulus signal is outputted under a set stimulus condition.

Figure 3:
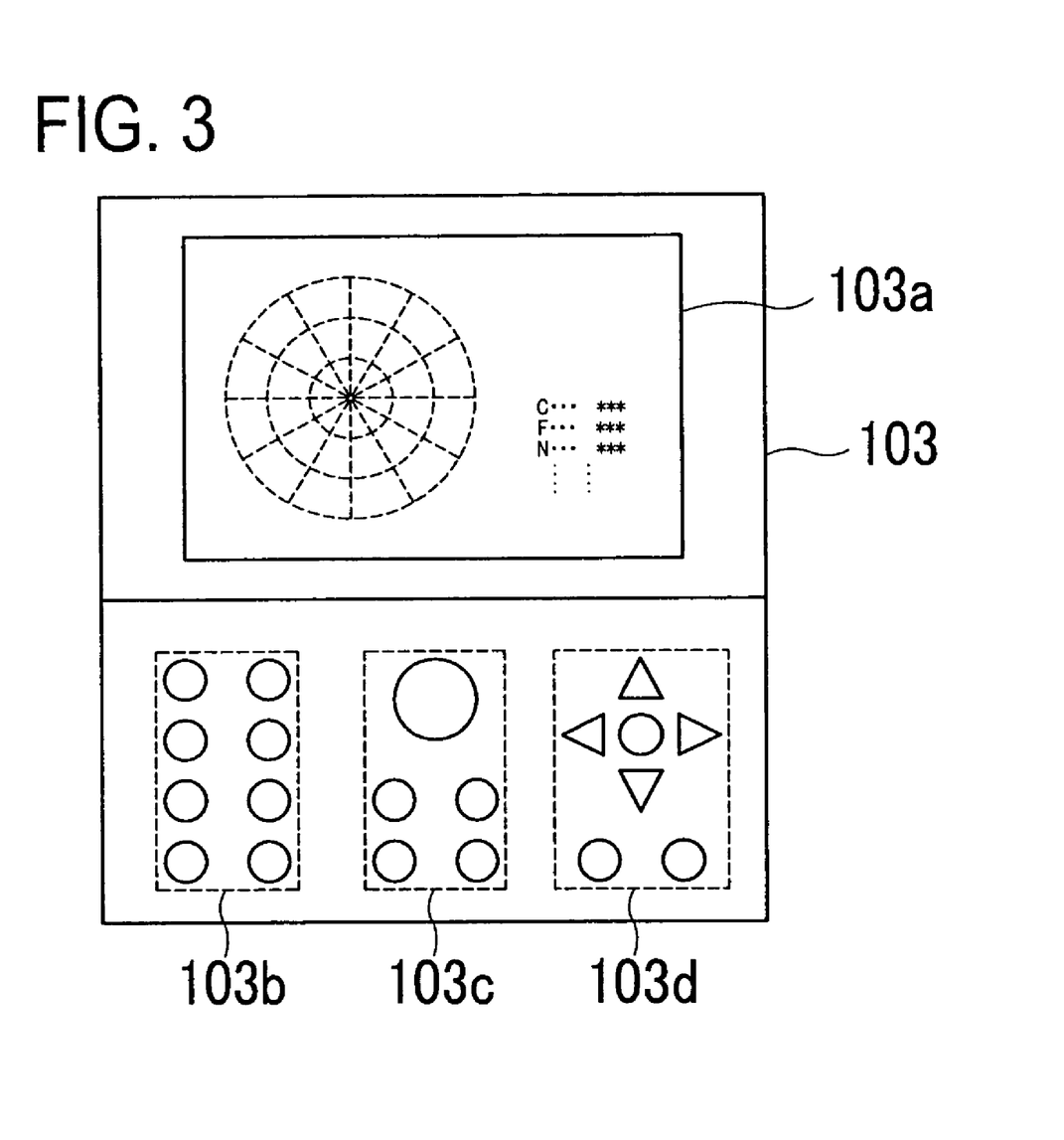
FIG. 3 is a schematic configuration view of a setting part for setting an output condition of an electric stimulus pulse signal.

FIG. 3 is a schematic configuration view of the setting part 103. A display (a display part) 103a displays the set stimulus condition, the appearance positions of phosphenes, etc. An electrode designating part 103b has operation buttons (the input part) for designating the electrode(s) from which stimulus signal(s) is/are to be outputted. A stimulus condition setting part 103c has operation buttons (the input part) including a dial for setting an output condition (a stimulus condition) of the stimulus signal(s) to be outputted from the designated electrode(s). A phosphene recording part 103d has operation buttons (the input part) including a joystick for recording what position in the visual field of the patient the phosphene(s) appears by the stimulus signal(s) outputted from the designated electrode(s) under the set stimulus condition.

The storage part 104 stores a plurality of combinations of the stimulus conditions and others set by the setting part 103 and the appearance positions of the corresponding phosphenes and others.

Preferably, the external unit 13 has a portable size for the patient. The setting part 103 may be built in the external unit 13 or arranged as a separate unit.

The primary coil 14 transmits the data for stimulus signal converted in the processing unit 100 (the signal converting part 102) and electric power (data for power) form the power supply unit 110, in the form of electromagnetic waves to the intracorporeal device 20. At the center of this primary coil 14, a magnet not shown is attached to be used for fixing the position thereof with respect to a secondary coil 21 mentioned later.

The intracorporeal device 20 includes the secondary coil (a receiving unit) 21, a process control part 22, a plurality of needlelike electrodes 23 each having a pointed distal end, and an indifferent electrode 30. The secondary coil 21 and the process control part 22 are connected to each other by a conductive wire (a signal line) 25. The process control part 22 are connected to each electrode 23 and the indifferent electrode 30 by conductive wires (signal lines) 24. In this embodiment, a distal end portion of each conductive wire 24 is used as the electrode 23. As an alternative, an electrode 23 separately produced from and joined to the conductive wire 24 may be used.

The secondary coil 21 receives electromagnetic waves from the extracorporeal device 10 (the primary coil 14). At the center of this secondary coil 21, a magnet not shown is attached to be used for fixing the position thereof with respect to the primary coil 14.

The process control part 22 divides the waves received by the secondary coil 21 into the data for stimulus signal and the electric power, converts the data for stimulus signal into the stimulus signal (generates the stimulus signal), and distributes and outputs the stimulus signal from the electrodes 23.

Each conductive wire 24 (and each electrode 23) is made of a material exhibiting good biocompatibility and corrosion resistivity, and having conductivity, such as gold, platinum, etc. This is coated with resin exhibiting good biocompatibility and insulation such as polyimide, poly-para-xylylene, parylene, silicone, etc.

Figure 4A:
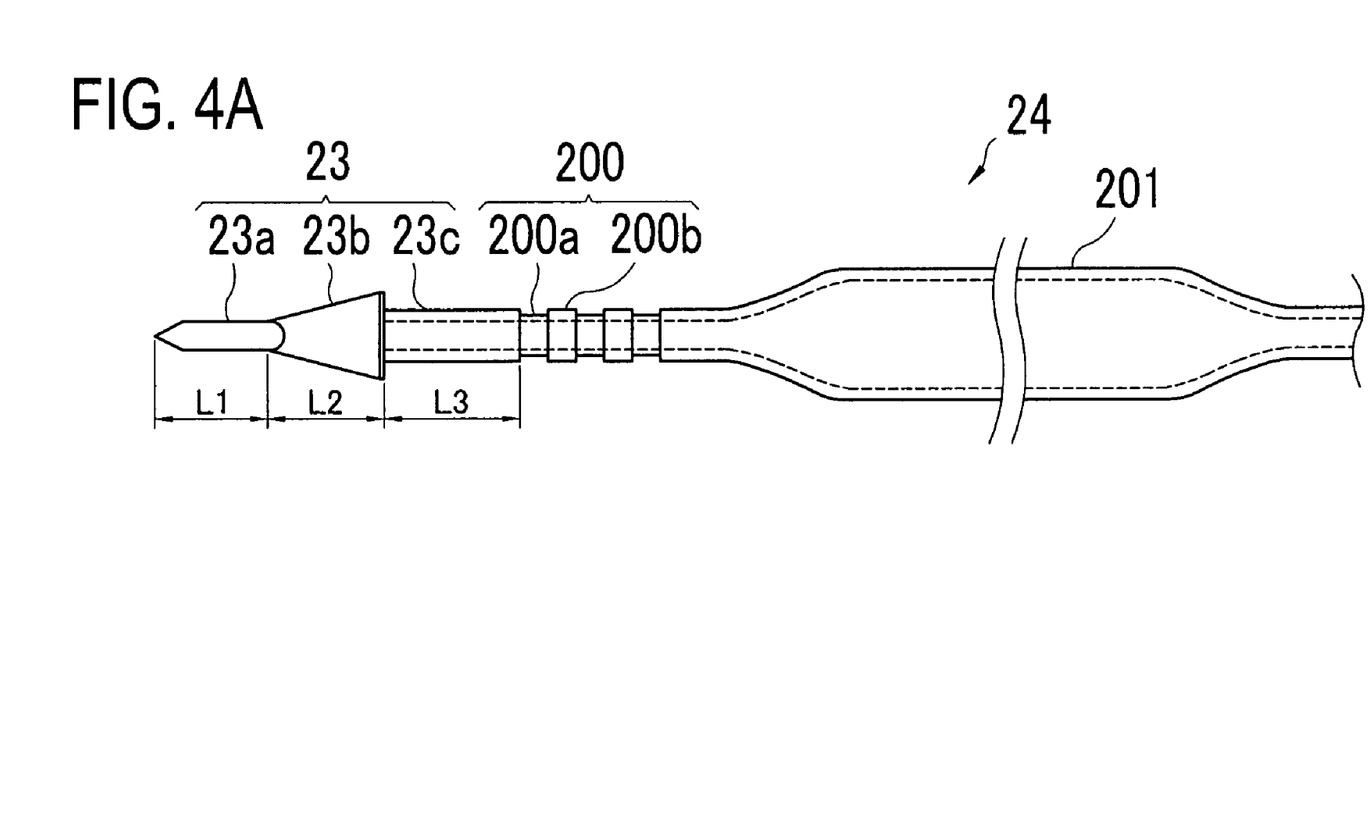
FIG. 4A is a schematic configuration view of an electrode and a conductive wire.
Figure 4B:
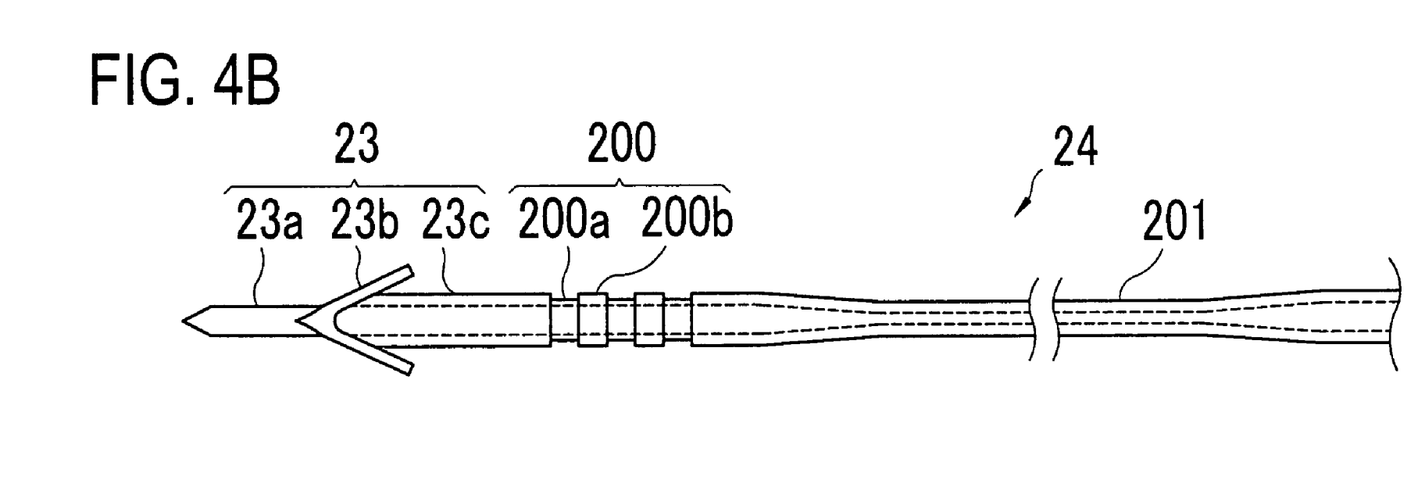
FIG. 4B is a schematic configuration view of the electrode and the conductive wire.

FIGS. 4A and 4B are schematic configuration views of the electrode 23 and the conductive wire 24; FIG. 4A is a top view and FIG. 4B is a side view. Each electrode 23 includes an electrode portion 23a, a retaining portion 23b, and an implanted portion 23c.

The electrode portion 23a is a leading end portion of the conductive wire 24 and uncoated with the aforementioned resin and formed in a pointed needle shape easy to stick in the optic papilla. The diameter of this electrode portion 23a (i.e., the diameter of the conductive wire 24) is preferably about 10 μm to about 200 μm, more preferably about 30 μM to about 100 μm. If the diameter of the electrode portion 23a is less than 10 μm, it is hard to stick in the optic papilla. If the diameter of the conductive wire 24 exceeds 200 μm, it is too rigid to easily handle. The length L1 of the electrode portion 23a has only to be long enough to electrically stimulate the nerve fibers. It is appropriately determined based on a material and a surface area of the electrode 23 (the conductive wire 24). It is preferably about 200 μm to about 2 mm and more preferably about 400 μm to about 1 mm. In this embodiment, the material of the conductive wire 24 (the electrode 23) is platinum, the diameter of the electrode portion 23a is 50 μm, and the length of the electrode portion 23a is 500 μm.

The retaining portion 23b is made of the aforementioned resin and used to prevent the electrode 23 from coming off after the electrode 23 is inserted in the optic papilla. In this embodiment, the retaining portion 23b has such a wedged shape (V shape) that a pair of wings facing each other gradually widen from the distal end side with respect to the electrode portion 23a. This shape makes it possible to prevent damages to tissues when the electrode 23 is stuck therein and to generate resistance in a pull-out direction. Furthermore, the length L2 of the retaining portion 23b has only to be long enough to make the electrode 23 hard to unstick after inserted in the optic papilla but so long as not to protrude from the optic papilla while the electrode portion 23a is located at a predetermined depth. It is preferably about 100 μm to about 1 mm and more preferably about 300 μm to about 800 μm. In this embodiment, the length of the retaining portion 23b is 500 μm.

The implanted portion 23c is used to keep an electrode discrimination portion 200 mentioned later outside the optic papilla when the electrode 23 is inserted in the optic papilla and also used to for depth adjustment to place the electrode portion 23a at the predetermined depth in the optic papilla. Such implanted portion 23c is coated with the aforementioned resin and the length L3 thereof has only to be long enough to place the electrode portion 23a at the predetermined depth in the optic papilla.

The conductive wire 24 is formed with the electrode discrimination portion 200 and a flat portion 201 for limiting an elastic force of the conductive wire 24 with respect to the electrode 23 to thereby facilitate handling of the electrode 23 during surgery. The electrode discrimination portion 200 is constituted of a combination of recesses 200a formed by partially removing the resin coating the conductive wire 24 by a predetermined amount and at fixed intervals and protrusions 200b formed between the recesses 200a. Such electrode discrimination portion 200 is formed in each of the electrodes 23 with different numbers of the recesses 200a and/or the protrusions 200b, thereby enabling discrimination of each electrode 23. The flat portion 201 is formed by flattening a predetermined region of the conductive wire 24. The electrode 23 has to have the thickness (the diameter) capable of being inserted in the optic papilla. To the contrary, the conductive wire 24 if having such thickness (diameter) has such a large elastic force as to make it difficult to handle the electrode 23. Therefore, the flat portion 201 is provided to facilitate handling of the electrode 23 during insertion (implantation). This flat portion 201 is preferably formed in a place as closer to the electrode 23 side as possible in order to facilitate the handling of the electrode 23 and also prevent the electrode 23 from coming off from the optic papilla. The electrode discrimination portion 200 has only to be formed in a place where it is ascertainable even when the electrode 23 is inserted in the optic papilla.

Figure 5A:
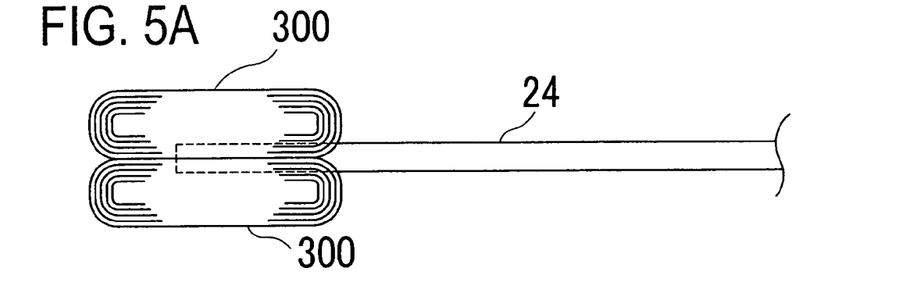
FIG. 5A is a view showing a process of producing the electrode.

FIGS. 5A to 5D are views showing a process of producing the electrode 23. As shown in FIG. 5A, firstly, two masking members 300 each of which is made of a soft and foldable material such as parafilm wound in a roll shape are pressure-bonded to each other by interposing the leading end portion of the conductive wire 24 therebetween. Each masking member 300 is also used for forming the retaining portion 23b and therefore has at least a required length to form the retaining portion 23b in a lateral width (in a direction perpendicular to the drawing sheet).

Figure 5B:
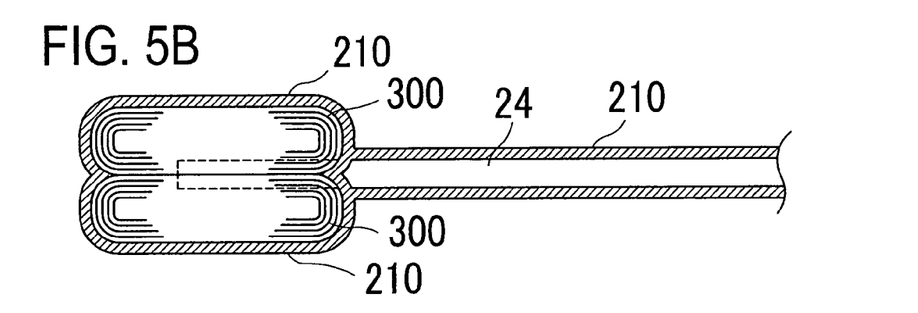
FIG. 5B is another view showing the process of producing the electrode.

Subsequently, the entire conductive wire 24 is coated with resin exhibiting good biocompatibility and insulation while the masking members 300 are press-bonded as shown in FIG. 5B, thereby forming a coating layer 210. The film thickness of the coating layer 210 has only to be thick enough to sufficiently coat the conductive wire 24 to prevent infiltration of body fluid and others. It is preferably about 1 µm to about 20 µm and more preferably about 3 µm to about 15 µm. Prior to coating, the predetermined region of the conductive wire 24 is pressed and flattened in advance by a roller or the like to form the aforementioned flat portion 201. In this embodiment, parylene is used as the coating resin and its film thickness is 10 µm.

Figure 5C:
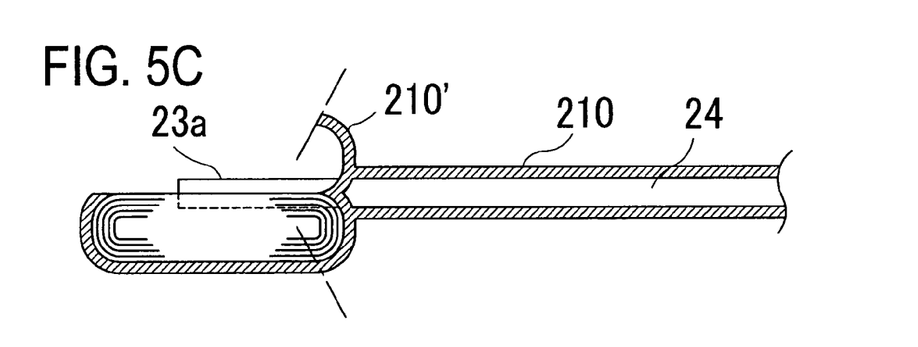
FIG. 5C is another view showing the process of producing the electrode.
Figure 5D:
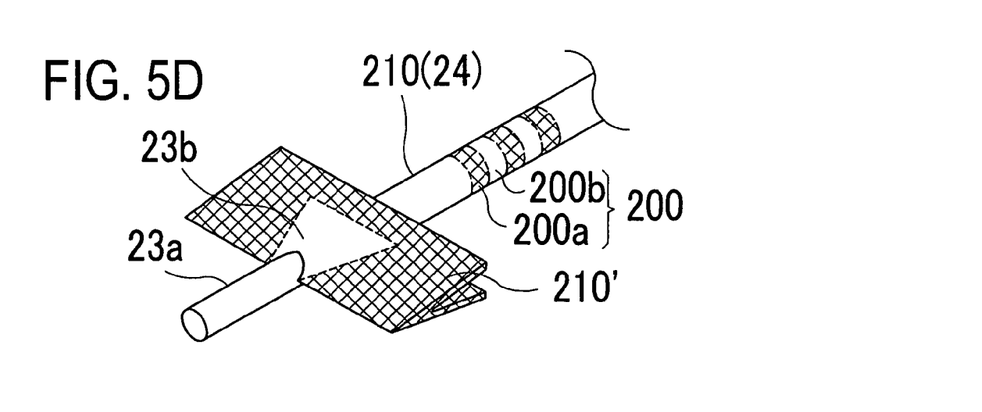
FIG. 5D is another view showing the process of producing the electrode.

As shown in FIG. 5C, successively, each masking member 300 is cut in a widthwise direction at a predetermined position (a position indicated by a dashed line in the figure) and all the masking members 300 are removed. The coating layer 210' left after removal of all the masking members 300 is used as a main body forming the retaining portion 23b as shown in FIG. 5D. By such removal of the masking members 300, the leading end portion of the conductive wire 24 becomes the electrode portion 23a uncoated with resin (exposed). A distal end of the electrode portion 23a may be sharpened prior to coating or after coating.

Then, the remaining coating layer 210' is cut away by excimer laser or the like as shown in FIG. 5D, thereby forming the turn-back retaining portion 23b. When the coating layer 210 is removed from the conductive wire 24 by the excimer laser or the like, the electrode discrimination portion 200 constituted of a combination of the recesses 200a and the protrusions 200b is formed. Each recess 200a is formed by thinning the film thickness of the coating layer 210 to the degree that enables discrimination of the recess 200a without cutting off the whole coating layer 210 to expose the conductive wire 24. For the coating layer 210 having a film thickness of about 10 µm, for example, each recess 200a is formed so that the film thickness becomes about 5 µm. In this embodiment, the electrode discrimination portion 200 is constituted of a combination of the recesses and the protrusions but not limited to such configuration. The electrode discrimination portion 200 has only to enable individual discrimination of the electrode 23 by the surface of the conductive wire 24 located outside the optic papilla (in a vitreous body) after the electrode 23 is inserted in the optic papilla. For instance, after the coating layer 210 is formed on the conductive wire 24, a protrusion may be formed of good biocompatible resin or the like on the coating layer 210.

As above, the retaining portion 23b is formed integral with the coating layer 210 coating the conductive wire 24 and hence is unlikely to come off during surgery and others. Since the retaining portion 23b is made of resin, it is adequately soft and can prevent damages to the tissues. Of course, the retaining portion 23b may be formed separately from the coating layer 210 and bonded to the conductive wire 24 with good biocompatible adhesion or the like.

The intracorporeal device 20 excepting the electrode portion 23a is entirely coated with resin or the like exhibiting good biocompatibility and insulation as mentioned above. The plurality of conductive wires 24 are wrapped together by a tube 26 formed of a good-biocompatible and flexible material such as silicone.

The intracorporeal device 20 is placed (implanted) in the body of the patient by surgery in advance. For instance, the secondary coil 21 and the process control part 22 are placed (implanted) under the skin of a temporal region of the patient as shown in FIG. 1. The primary coil 14 is placed on the skin in a position that faces the secondary coil 21.

Figure 6A:
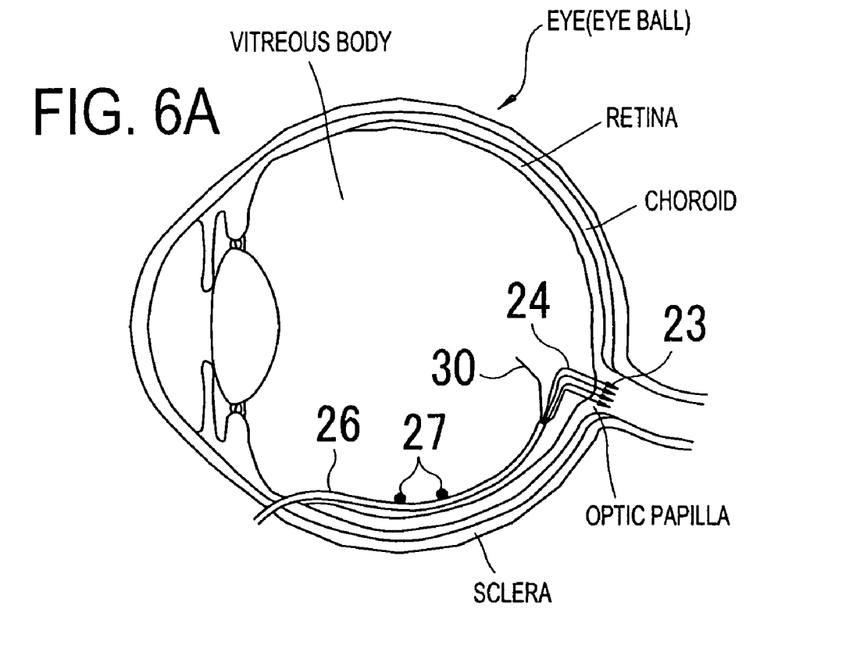
FIG. 6A is a view showing a placed state of the electrodes.
Figure 6B:
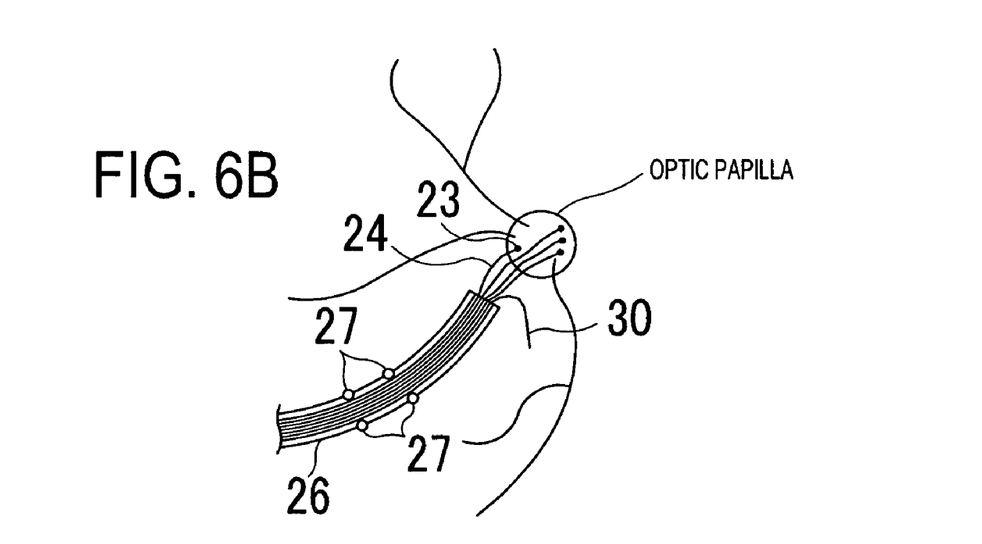
FIG. 6B is another view showing the placed state of the electrodes.

On the other hand, the electrodes 23 are directly inserted and placed (implanted) in the optic papilla at which nerve fibers concentrate. FIGS. 6A and 6B are views showing a placed state of the electrodes 23; FIG. 6A is a horizontal cross-section view of an entire eye ball and FIG. 6B is an enlarged view of the optic papilla and its surrounding. The tube 26 binding the conductive wires 24 together is stuck in the eyeball through a hole formed in a sclera and inserted along a retina to reach the vicinity of the optic papilla. The electrode 23 formed in (or connected to) the leading end of each conductive wire 24 extending out of the end of the tube 26 is inserted and placed (implanted) at a predetermined depth in a position avoiding interference with blood vessels of the optic papilla. To stick the electrodes 23 in the optic papilla, a needlelike piercing tool may be used.

Figure 7:
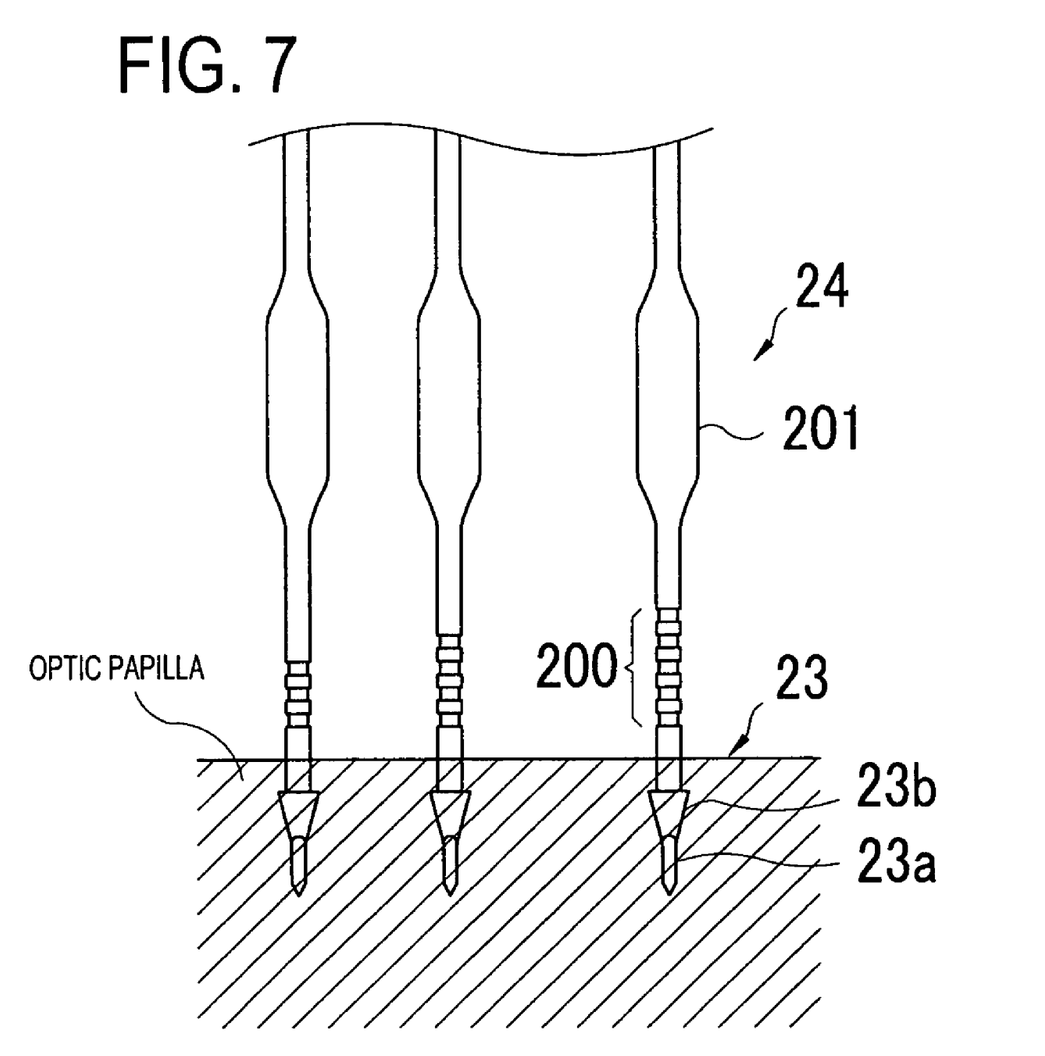
FIG. 7 is another view showing the placed state of the electrodes.

As shown in FIG. 7, each electrode 23 inserted in the optic papilla is hard to come off owing to each retaining portion 23b and restriction (reduction) of the elastic force resulting from the shape of the flat portion 201. By the electrode discrimination portions 200, the inserted electrodes 23 can be individually discriminated. The tube 26 is fixed in the eye by tacks 27. The indifferent electrode 30 is kept staying in the vitreous body. It is to be noted that the indifferent electrode 30 may be placed (implanted) in the optic papilla.

Next, operations for regenerating the sight will be explained.

The device 1 is arranged to output the stimulus signals from the electrodes 23 placed in the optic papilla to make phosphenes appear in the visual field of the patient, thereby allowing the patient to obtain the sight. For previous preparation, while the intracorporeal device 20 is placed in the patient, the setting part 103 is used to check the appearance positions and shapes of the phosphenes specific to the patient under various stimulus conditions. Firstly, by use of the electrode designating part 103b, it is set whether the stimulus signal is outputted from a single electrode 23 or the stimulus signals are simultaneously outputted from the plurality of electrodes 23. For simultaneous output from the plurality of electrodes 23, furthermore, a combination of the electrodes 23 from which the stimulus signals are to be outputted at the same time is set. In this embodiment, the simultaneous output from the plurality of electrodes also includes output of the stimulus signals at different timings within a very short time as well as output of the stimulus signals at exactly the same timing.

Subsequently, by use of the stimulus condition setting part 103c, an output condition (a stimulus condition) of the stimulus signal to each of the electrodes 23 is set. In the setting part 103c, a current value, a frequency, a pulse width, the number of pulses, a halt time between pulses, a pulse waveform (a single-phase wave or a double-phase wave), a charge quantity, etc. can be set individually. The set details are displayed on the display 103a. In the case of selecting the double-phase wave, the pulse waveform can be set to a symmetric double-phase rectangular wave or an asymmetric double-phase rectangular wave. In the case of setting the asymmetric double-phase rectangular wave, furthermore, a waveform condition of a next anode is set so that a pulse height (a current value) is lower and a pulse width is longer than a waveform condition of a cathode to provide a balance.

Figure 8:
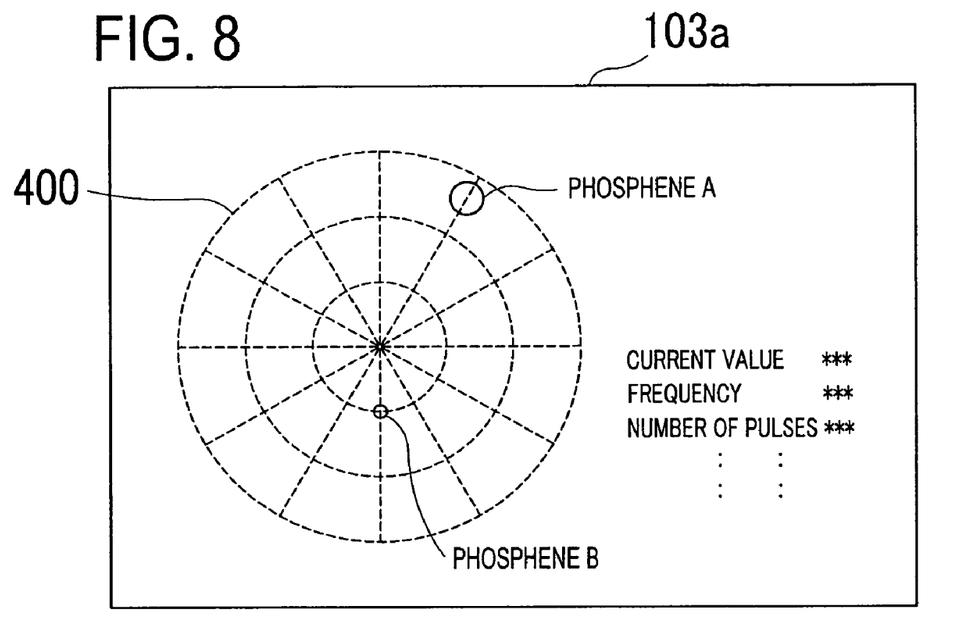
FIG. 8 is a view showing an example in which appearance positions of phosphenes are displayed on a chart and recorded.

Thereafter, by use of a stimulus start button not shown, the electrode(s) 23 is/are caused to output the stimulus signal(s) under the set stimulus condition. It is then checked at what position within the visual field of the patient and in what shape (how large) the phosphene appears. As shown in FIG. 8, a chart 400 for recording the appearance position and the shape of a phosphene is displayed on the display 103a. By use of the phosphene recording part 103d, the appearance position and the shape of a phosphene are recorded on the chart 400.

For instance, if the patient indicates the appearance position of a phosphene as "a coin-sized one appears at 1 o'clock position from the center of the visual field to the outside", a phosphene A is displayed and recorded at a position on the chart 400 considered as corresponding to such indication by use of the recording part 103d. When the stimulus signal is outputted under a different stimulus condition and others, if the patient indicates that "a match-head-sized one appears at 6 o'clock position from the center of the visual field to the inside", a phosphene B is displayed and recorded at a position on the chart 400 considered as corresponding to such indication.

As above, until the appearance positions of the phosphenes over a wide range in the visual field of the patient are confirmed, the stimulus signals are outputted under different stimulus conditions and others for mapping the phosphenes on the chart 400. After the appearance positions of the phosphenes over an expected wide range in the visual field are confirmed, they are stored (saved) in the storage part 104 by a save button not shown. In the storage part 104, the appearance position and the shape of each phosphene and the corresponding stimulus condition and others are stored in association with each other.

After the above previous preparation is conducted, the device 1 is operated. Image data on the object captured by the photographing unit 12 is transmitted to the processing unit 100. The control part 101 transmits the received image data and the appearance positions and shapes of phosphenes specific to the patient stored in the storage part 104 to the signal converting part 102. Based on the received image data and the appearance positions and shapes of phosphenes, the signal converting part 102 extracts the appearance positions and shapes of phosphenes required for the patient to recognize the image (the object), sets the stimulus condition associated with this, and converts the image data into data for stimulus signal based on the set stimulus condition. The control part 101 transmits the data for stimulus signal by the signal converting part 102 to the intracorporeal device 20 through the primary coil 14.

The process control part 22 receives the data for stimulus signal transmitted from the extracorporeal device 10 (the primary coil 14) through the secondary coil 21, converts it into a stimulus signal(s), and outputs the stimulus signal(s) from the electrode(s) 23. The stimulus signal(s) outputted from the electrode(s) 23 passes through the optic nerve from the optic papilla to stimulate the brain. Thus, the patient perceives the phosphenes appearing in the visual field and obtains the sight (vision). In the device of the present embodiment, as mentioned above, electric stimulus is given from the optic papilla at which nerve fibers concentrate and hence the phosphenes can be made to appear over a wide range in the visual field of the patient. As a result, the patient can obtain the sight over a wide range.

While the presently preferred embodiment of the present invention has been shown and described, it is to be understood that this disclosure is for the purpose of illustration and that various changes and modifications may be made without departing from the scope of the invention as set forth in the appended claims.

The invention claimed is:

1. A sight regeneration assisting device for regenerating sight of a patient, the sight regeneration assisting device comprising:
    a plurality of needlelike electrodes, each electrode having a pointed distal end and configured to be inserted into an optic papilla of a patient's eye in use;
    a signal generator configured to generate an electric stimulus pulse signal be outputted from the plurality of needlelike electrodes;
    a plurality of conductive wires configured to connect the plurality of needlelike electrodes to the signal generator, each conductive wire having a rigid portion and a flat portion extending along its axial direction, the rigid portion having a cross-sectional thickness so as to be sufficiently rigid to permit insertion of the electrode into the optic papilla, and the flat portion configured to be placed in a vitreous body of the patient's eye when the electrode is inserted into the optic papilla and having a cross-sectional thickness less than the cross-sectional thickness of the rigid portion; and
    a turn-back retaining portion formed in the electrode at a predetermined distance in a proximal direction from the pointed distal end of the electrode and in a predetermined position on the electrode.

2. The sight regeneration assisting device according to claim 1, wherein:
the electrode, except for a portion at a distal end of the electrode, is coated with a coating layer made of a resin exhibiting good biocompatibility and insulation;
the turn-back retaining portion is made of the resin; and
the turn-back retaining portion is integrally formed with the coating layer.

3. The sight regeneration assisting device according to claim 1, wherein each conductive wire includes a structure for electrode discrimination that is configured to be placed in the vitreous body when the electrode is inserted into the optic papilla.

4. The sight regeneration assisting device according to claim 3, wherein
each conductive wire is coated with a coating layer made of a resin exhibiting good biocompatibility and insulation, and
the structure for electrode discrimination is formed by coating each conductive wire with the coating layer.

5. The sight regeneration assisting device according to claim 1, wherein the turn-back retaining portion is configured to prevent removal of the electrode from the optic papilla.

* * * * *